US008470331B2

(12) United States Patent
Wheeler et al.

(10) Patent No.: US 8,470,331 B2
(45) Date of Patent: Jun. 25, 2013

(54) COMPOSITION OF ANTIGEN AND GLYCOLIPID ADJUVANT FOR SUBLINGUAL ADMINISTRATION

(75) Inventors: Alan W. Wheeler, Worthing (GB); Gary Elliott, Pacifica, CA (US); Christopher Cluff, Hamilton, MT (US)

(73) Assignee: Allergy Therapeutics (UK) Limited, West Sussex (GB)

( * ) Notice: Subject to any disclaimer, the term of this patent is extended or adjusted under 35 U.S.C. 154(b) by 1316 days.

(21) Appl. No.: 10/181,684

(22) PCT Filed: Jan. 15, 2001

(86) PCT No.: PCT/GB01/00142
§ 371 (c)(1),
(2), (4) Date: Nov. 19, 2002

(87) PCT Pub. No.: WO01/51082
PCT Pub. Date: Jul. 19, 2001

(65) Prior Publication Data
US 2003/0165512 A1 Sep. 4, 2003

(30) Foreign Application Priority Data
Jan. 14, 2000 (GB) .................................. 0000891.2

(51) Int. Cl.
*A61K 39/00* (2006.01)
(52) U.S. Cl.
USPC ..................................... 424/184.1; 424/278.1
(58) Field of Classification Search
USPC ....................................................... 424/184.1
See application file for complete search history.

(56) References Cited

U.S. PATENT DOCUMENTS

| 3,541,201 | A |   | 11/1970 | Brown ............................... 424/7 |
| 3,792,159 | A |   | 2/1974  | Green et al. |
| 4,070,455 | A |   | 1/1978  | Green et al. |
| 4,258,029 | A |   | 3/1981  | Moloney et al. |
| 4,855,283 | A |   | 8/1989  | Lockhoff et al. |
| 4,912,094 | A |   | 3/1990  | Myers et al. |
| 4,956,489 | A |   | 9/1990  | Auriol et al. |
| 4,975,420 | A |   | 12/1990 | Silversides et al. |
| 4,987,237 | A |   | 1/1991  | Myers et al. |
| 5,244,663 | A | * | 9/1993  | Bruttmann et al. ........... 424/400 |
| 5,750,110 | A |   | 5/1998  | Prieels et al. |
| 5,762,943 | A |   | 6/1998  | Dolovich et al. |
| 5,776,468 | A |   | 7/1998  | Hauser et al. |
| 5,795,862 | A |   | 8/1998  | Frank et al. |
| 5,973,128 | A | * | 10/1999 | Lingwood et al. ............. 536/4.1 |
| 5,997,873 | A | * | 12/1999 | Srivastava .................. 424/193.1 |
| 6,146,632 | A |   | 11/2000 | Momin et al. |
| 2001/0021384 | A1 |   | 9/2001  | Jourdier et al. |
| 2003/0007977 | A1 |   | 1/2003  | Wheeler et al. |
| 2005/0123570 | A1 |   | 6/2005  | Ulrich et al. |

FOREIGN PATENT DOCUMENTS

| CA | 2424160 A1 | 8/2000 |
| EP | 0239400 | 8/1994 |
| EP | 0640347 A1 | 3/1995 |
| EP | 0182442 | 4/1996 |
| EP | 0737072 A1 | 10/1996 |
| EP | 0988862 A3 | 9/1999 |
| EP | 1031347 B1 | 4/2002 |
| GB | 1128637 | 9/1968 |
| GB | 1377074 | 12/1974 |
| GB | 1492973 | 11/1977 |
| GB | 2220211 | 1/1990 |
| WO | WO 92/16556 | 10/1992 |
| WO | 9420070 A1 | 9/1994 |
| WO | WO 94/27636 | 12/1994 |
| WO | WO 95/05850 | 3/1995 |
| WO | WO 95/17209 | 6/1995 |
| WO | WO 96/25664 | 8/1996 |
| WO | WO 96/34626 | 11/1996 |
| WO | 9840097 A2 | 9/1998 |
| WO | WO 98/43670 | 10/1998 |
| WO | WO 98/44947 | 10/1998 |
| WO | WO 98/58956 | 12/1998 |
| WO | WO 99/10375 | 3/1999 |
| WO | WO 99/16884 | 4/1999 |
| WO | WO 99/24577 | 5/1999 |
| WO | WO 99/64074 | 12/1999 |
| WO | WO 99/66043 | 12/1999 |
| WO | 0000218 A1 | 1/2000 |
| WO | WO 00/29582 | 5/2000 |
| WO | WO 00/50078 | 8/2000 |
| WO | WO 00/62801 | 10/2000 |
| WO | WO 00/65058 | 11/2000 |
| WO | 0076476 A1 | 12/2000 |
| WO | WO 00/72876 | 12/2000 |
| WO | WO 00/78353 | 12/2000 |
| WO | 0213858 A1 | 2/2001 |
| WO | 0129214 A1 | 4/2001 |
| WO | WO 01/929214 | 4/2001 |
| WO | 0195914 A1 | 12/2001 |

OTHER PUBLICATIONS

Chauncey et al., J. Dental Res, 33(3):321-334, 1954.*
Chauncey et al., J. Am. Dental. Assoc. 63:42-50, 1961.*
Lindquist et al., Enzyme, 20:166-175, 1977.*
Tan et al., Hum. Heredity vol. 26:207-216, 1976.*
Lindquist et al., Enzyme, 20:277-291, 1975.*
Verhoef et al., Eur J. Of Drug Met. Pharm. 15(2):83-93, 1990.*
Valdez et al., Dig. Dis. 9:125-132, 1991.*
Sasaki et al. (1998), "Comparison of Intranasal and Intramuscular Immunization Against Human Immunodeficiency Virus Type 1 with a DNA-Monophosphoryl Lipid A Adjuvant Vaccine," *Infection and Immunity* 66(2):823-826.
Schneerson et al. (1991), "Evaluation of Monophosphoryl Lipid a MPL as an Adjuvant Enhancement of the Serum Antibody Response in Mice to Polysaccharide-Protein Conjugates by Concurrent Injection with MPL," *Journal of Immunology* 147(7):2136-2140.

(Continued)

*Primary Examiner* — Yunsoo Kim
(74) *Attorney, Agent, or Firm* — Karen Canaan; CanaanLaw, P.C.

(57) ABSTRACT

A method of producing a mucosal and systemic immune response in a mammal comprising administering sublingually an effective amount of a composition comprising at least one antigen and a glycolipid adjuvant to said mammal.

7 Claims, No Drawings

OTHER PUBLICATIONS

Cox, et al., "Adjuvants—A Classification and Review of Their Modes of Action", Vaccine (1997) 15(3):248-256.
Holen et al. "Specific T cell lines for ovalbumin, ovomucoid, lysozyme and two OA synthetic epitopes, generated from egg allergic patients' PBMC," Clin. Exp. Allerg. (1996) 26:1080-1088, abstract.
Hoyne et al., "Peptide-mediated regulation of the allergic immune response," Immunol. Biol. (1996) 74:180-186.
Ngo et al. (1994), The Protein Folding Problem and Tertiary Structure Prediction, Mertz, Jr. et al. Eds., Birkhauser Boston, pp. 491-495.
Nixon-George, et al., "The Adjuvant Effect of Stearyl Tyrosine on a Recombinant Subunit Hepatitis B Surface Antigen", J. Immunol. (1990) 144(12):4798-4802.
Penney, et al., Further Studies on the Adjuvanticity of Stearyl Tyrosine and Ester Analogues, Vaccine (1993) 11:1129-1134.
Scalzo et al., "Induction of Protective Cytotoxic T Cells to Murine Cytomegalovirus by Using a Nonapeptide and a Human-Compatible Adjuvant," (1995) J. Virol. 36(2):1306-1309.
Ulrich and Myers, "Monophosphoryl Lipid A as an Adjuvant. Past Experiences and New Directions," Vaccine Design: The Subunit and Adjuvant Approach (Powell & Newman, eds., Plenum Press, N.Y. 1995).
Wheeler, et al., "L-Tyrosine as an Immunological Adjuvant," (1982) Int. Archs Allergy Appl. Immun. 69:113-119.
Vourdas et al., "Double-blind, placebo-controlled evaluation of sublingual immunotherapy with standardized olive pollen extract in pedriatric patients with allergic rhinoconjuntivitis and mild asthma due to olive pollen sensitization," Allergy 53:662-672 (1998).
Marsh, Preparation and Properties of "Allergoids" Derived from Native Pollen by Mild Formalin Treatment, Int. Arch. Allergy 41:199-215 (1971).
Allergy Therapeutics Pollinex Quattro® Brochure (1999).
Drachenberg et al., A Well-Tolerated Grass Pollen-Specific Allergy Vaccine Containing a Novel Adjuvant, Monophosphoryl lipid A, reduces allergic Symptoms After only Four Preseasonal Injections, Allergy 498-505 (2001).
Wheeler et al., A Th1-Inducing Adjuvant, MPL®, Enhances Antibody Profiles in Experimental Animals Suggesting It Has the Potential to Improve the Efficacy of Allergy Vaccines, Int. Arch. Allergy Immunol 126:135-139 (2001).
Van Ginkel, Vaccines for Mucosal Immunity to Combat Emerging Diseases, Emerging Infectious Diseases 6(2): 123-132 (2000).
Ribi Adjuvant Fact Sheet (2003).
Akahira-Azuma et al., Early Delayed-Type Hypersensitivity Eosinophil Infiltrates Depend on T Helper 2 Cytokines and Interferon-Gamma via CXCR3 Chemokines, Immunology 111:306-317 (2004).
Cleland et al., The Development of Stable Protein Formulations: A Close Look at Protein Aggregation, Deamidation and Oxidation, Critical Reviews in Therapeutic Drug Carrier Systems 10(4):307-377 (1993).
Dalton et al.,The Solubilities of Certain Amino Acids in Water, the Densities of Their Solutions At Twenty-five Degrees, and the Calculated Heats of Solution and Partial Molal Volumes, J. Biol. Chem. 103(2):549-576 (1933).
Dearman et al., Divergent Antibody Isotype Responses Induced in Mice by Systemic Exposure to Proteins: a Comparison of Ovalbumin with Bovine Albumin, Food and Chemical Toxicology 38:351-360 (2000). Dunn et al., the Solubility of the Amino Acids in Water, The Journal of Biological Chemistry pp. 579-595 (1933).
Dehlink et al., Absence of Systemic Immunologic Changes During Dose Build-up Phase and Early Maintenance Period in Effective Specific Sublingual Immunotherapy in Children, Clinical and Experimental Allergy 36:32-39 (2006).
Drachenberg et al., Short-Term Immunotherapy with Tree Pollen Allergoids and the Adjuvant Monophosphoryl A—Results from a Multi-Centre, Placebo-Controlled Randomised, Double-Blind Study, Allergologie 25(9):466-474 (2002).
Drachenberg et al., Short-Term Immunotherapy Using an Allergy Vaccine Adjuvanted with Monophosphoryl Lipid A: A Post-Marketing Surveillance Study, Int. Rev. Allergol. Clin. Immunol. 8(4):219-223 (2002).
Drachenberg et al., Efficacy and Tolerability of Short-Term Specific Immunotherapy with Pollen Allergoids Adjuvanted by Monophosphoryl Lipid A (MPL) for Children and Adolescents, Allergol Et Immunopathol 31 (5):270-277 (2003).
Dunn et al., The Solubility of the Amino Acids in Water, J. Biol. Chem. 103(2):579-595 (1933).
Garren et al., Buccal Drug Absorption. I. Comparative Levels of Esterase and Peptidase Activities in Rat and Hamster Buccal and Intestinal Homogenates, Int'L J. Pharmaceutics 48:189-194 (1988).
Gonzalez-Hernandez et al., Peripheral Blood CD161+T Cells from Asthmatic Patients are Activated During Asthma Attack and Predominantly Produce IFN-Gamma Scand, J. Immunol. 65:368-375 (2007).
Hertl et al., Immunologic Mechanisms in Hypersensitivity Reactions to Metal Ions: an Overview, Allergy 55:108-115 (2000).
Jackson et al., Reduction of Human Anti-Tetanus Toxoid Antibody in hu-PBL-SCID mice by Immunodominant Peptides of Tetanus Toxoid, Clin Exp Immunol 137:245-252 (2004).
Johansen et al., Immunogenicity and Protective Efficacy of a Formalin-Inactivated Rotavirus Vaccine Combined with Lipid Adjuvants, Vaccine 21:368-375 (2003).
Mamessier et al., Cytokines in Atopic Diseases: Revisiting the Th2 Dogma, Eur. J. Dermatol. 16(2):103-113 (2006).
Marsh et al., Studies on "Allergoids" Prepared from Naturally Occurring Allergens, Immunology 18:705-722 (1970).
McCluskie et al., CpG DNA is an Effective Oral Adjuvant to Protein Antigens in Mice, Vaccine 19:950-957 (2001).
Moran et al., Chemical Modification of Crude Timothy Grass Extract (III) the Effect of Glutaraldehyde Induced Aggregation of Antigenic and Immunogenic Properties, Int. Arch. Allergy Appl. Immunol. 55:315-321 (1977).
Pajno et al., Clinical and Immunologic Effects of Long-term Sublingual Immunotherapy in Asthmatic Children Sensitized to Mites: A Double-Blind, Placebo-Controlled Study, Allergy 55:842-849 (2000).
Patel et al., Pollinex Quattro: A Novel and Well-Tolerated, Ultra Short-Course Allergy Vaccine, Expert. Rev. Vaccines 5(5):617-629 (2006).
Patterson et al., Polymerized Ragwee Antigen E(I) Preparation and Immunological Studies, J. Immunol. 110(5): 1402-1412 (1973).
Patterson et al., Polymerized Ragwee Antigen E(II) Preparation and Immunological Studies, J. Immunol. 110 (5):1413-1418 (1973).
Patterson et al., Polymerized Ragwee Antigen E(III) Preparation and Immunological Studies, J. Immunol. 112(5): 112:1855-1860 (1974).
Sri-Ram, Chemical Modification of Proteins and Their Significance in Enzymology, Immunochemistry, and Related Subjects, Advances in Enzymology: and Related Subjects of Biochemistry 24:105-160 (F.F. Nord, ed., John Wiley & Sons, 1962).
Stuck et al., Short-Term Preseasonal Immunotherapy with Birch Pollen Allergoid Plus Monosphosphorylipid a (MPL): Influence on Cytokine Production of Peripheral T Cells in Patients with Allergic Rhinitis, Allergy Clin Immunol Int—J World Allergy Org 16(2):60-64 (2004).
Vogel et al., Drug Discovery and Evaluation, Pharmacological Assays pp. 440-444 (1996).
Wheeler et al., Chemical Modification of Crude Timothy Grass Extract (II) Class and Specificity of Antibodies Induced by Chemically Modified Timothy Grass Pollen Extract, Int. Arch. Allergy Appl. Immunol. 50:709-728 (1976).
Yang et al., Mechanisms of Monophosphoryl Lipid A Augmentation of Host Responses to Recombinant HagB from Porphyromonas Gingivalis, Infection and Immunity 70(7):3557-3565 (2002).
Yssel et al., Regulatory T Cells and Allergic Asthma, Microbes and Infection (3) 899-904 (2001).
Zhou et al., Comparison of Enzyme Activities of Tissues Lining Portals of Absorption of Drugs Species Differences, Int'l J. Pharmaceutics 70(3):271-283 (1991) (Biosis Abstract).
Office Action for U.S. Appl. No. 11/040,952, dated Oct. 30, 2008, Double-Patenting Rejection.
Office Action for U.S. Appl. No. 11/040,952, dated Jul. 8, 2009, Double-Patenting Rejection.

Stearyl Tyrosine Information page, taken from Penney et al., A Simple Method for the Synthesis of Long-Chain Alkyl Esters of Amino Acids, J. Org. Chem. 50:1457-59 (1985).

MPL Structure page, taken from Hopkins et al., Allergol Et Immunopathol 29(6):245-254 (2001).

Azuma et al., Adjuvant Activity of Bacterial Glycolipids, Japan J. Microbiol. 20(5):465-468 (1976).

Baldridge et al., Monophosphoryl Lipid A Enhances Mucosal and Systemic Immunity to Vaccine Antigens Following Intranasal Administration, Vaccine 18:2416-2425 (2000).

Behling et al., Synthetic Glycolipid Adjuvants, J. Of Immunology, 117:847-851 (1976).

Childers et al., Adjuvant Activity of Monophosphoryl Lipid a for Nasal and Oral Immunization with Soluble or Liposome-Associated Antigen, Infect. Immun. 68:5509-5516 (2000).

Chu et al., CPG Oligodeoxynucleotides Act as Adjuvants that Switch on T Helper 1 (TH1) Immunity, J. Exp. Med. 186(10):1623-1631 (1997).

Fanta et al., Systemic Immunological Changes Induced by Administration of Grass Pollen Allergens via the Oral Mucosa During Sublingual Immunotherapy, Int. Arch. Allergy Immunol. 120(3):218-224 (1999).

Gorbach et al., New Glycolipids (chitooliogosaccharide derivatives) Possessing Immunostimulating and Antitumor Activities, Carbohydrate Research 260:73-82.

Holt et al., Sublingual Immunotherapy for Allergic Respiratory Diseases, Lancet 351:613-614 (1998).

Kanegasaki et al., Biological Activities of Analogues of Lipid a Based Chemically on the Revised Structural Model, Eur. J. Biochem. 143:237-242 (1984).

Kiyono et al., Lack of Oral Tolerance in C3H/HeJ Mice, J. Exp. Med. 155:605-610 (1982).

Leitner et al., Immune Responses Induced by Intramuscular or Gene Gun Injection of Protective Deoxyribonucelic Acid Vaccines that Express the Circumsporozoite Protein from Plasmodium Berghei Malaria Parasites, The Journal of Immunology 159(12):6112-6119 (1997).

Lockhoff, Glycolipids as Immunomodulators: Synthesis and Properties, Chem. Int. Ed. Engl. 20:1611-1620 (1991).

McCluskie et al., Route and Method of Delivery of DNA Vaccine Influence Immune Responses in Mice and Non-Human Primates, Molecular Medicine 5:287-300 (1999).

Pfaar et al., Sublingual Allergen-Specific Immunotherapy Adjuvanted with Monophosphoryl Lipid A: A PhaseI/IIa Study, Int. Arch. Allergy Immunol. 154:336-344 (2011).

Ponpipom et al., Glycolipids as Potential Immunologic Adjuvants, J. Med. Chem. 23:1184-1188 (1980).

Qureshi et al., Purification and Structural Determination of Nontoxic Lipid A Obtained from the Lipopolysaccharide of Salmonella Typhimurium, J. Bio. Chem. 257:11808-11815 (1982).

Razafindratsita et al., Improvement of Sublingual Immunotherapy Efficacy with a Mucoadhesive Allergen Formulation, J. Allergy Clin. Immunol. 120(2):278-285 (2007).

Slavkin, Changing Patterns of Disease and Mucosal Immunity, Jada 130:735-738 (1990).

Tomaki et al., Eosinophil Opoiesis in a Murine Model of Allergic Airway Eosinophilia: Involvement of Bone Marrow IL-5 and IL-5 Receptor-alpha, The Journal of Immunology 165:4040-4050 (2000).

Trolle et al., Intranasal Immunization with Protein-Linked Phosphorylcholine Protects Mice Against a Lethal Intranasal Challenge with Streptococcus Pneumoniae, Vaccine 18:2991-2998 (2000).

Van Wilsem et al., Oral Tolerance is Determined at the Level of Draining Lymph Nodes, Immunobiol. 194:403-414 (1995).

Wheeler et al., Studies in Experimental Animals showing that a TH1 enhancing adjuvant, MPL may have utility in Augmenting the efficacy of Allergy Vaccines, Joint 7th Annual Conference of the British Society of Immunology and British Society for Allergy and Clinical Immunology, Harrogate Abstract 193: 14-15 (1999).

Young et al., Production of Monoclonal Antibodies Specific for Two Distinct Steric Portions of the Glycolipid Ganglio-N-Triosylceramide (Asialo GM2), J. Exp. Med. 150:1008-1019 (1979).

Office Action for counterpart Canadian Application No. 2,397,359 dated Jan. 9, 2009, and Response to the Office Action filed with the Canadian Patent Office on May 21, 2009.

Interlocutory Decision Reversing Examiner for counterpart European Application No. 01942305.2 dated Dec. 14, 2011.

Grounds for Appeal of Decision Reversing Examiner in counterpart European Application No. 01942305.2 filed on Apr. 24, 2012.

Proprietor's Response to Grounds of Appeal of Decision Reversing Examiner in European Application No. 01942305.2 filed on Aug. 28, 2012.

* cited by examiner

US 8,470,331 B2

COMPOSITION OF ANTIGEN AND GLYCOLIPID ADJUVANT FOR SUBLINGUAL ADMINISTRATION

CROSS REFERENCE TO RELATED APPLICATIONS

This application claims priority under 35 U.S.C §119 to Great Britain Patent Application No. 0000891.2, filed Jan. 14, 2000.

FIELD OF THE INVENTION

The present invention relates to a method of producing a mucosal and systemic immune response using a sublingually administered formulation particularly, but not exclusively, for use in immunisation as a prophylactic or therapeutic vaccine, or in the treatment of allergy.

BACKGROUND OF THE INVENTION

The immune system has evolved specifically to detect and eliminate foreign or new material from a host. This material may be of viral, bacterial, or parasitic origin and may reside outside or within the cells of the host, or be of neoplastic origin. It may also be from other sources and not pathogenic or not intrinsically damaging to all subjects.

The mucosal immune system (MIS) consists of lymphoid tissues within and directly beneath the epithelial lining of the respiratory, genitourinary and gastrointestinal tract as well as beneath the ductal system of the salivary, lacrimal and mammary glands. The primary product of the MIS is IgA.

Vaccination is the best known and most successful application of an immunological principle to human health. Naturally, to be introduced and approved, a vaccine must be effective and the efficacy of all vaccines is reviewed from time to time. Many factors affect the efficacy of a vaccine. For example, a vaccine is usually administered by the subcutaneous or intramuscular route. Recently the sublingual route has been used for administration of therapeutic allergy vaccines. An effective vaccine must induce the appropriate immunity in terms of quantitative and qualitative effects and be stable on storage. With non-living vaccines in particular, it is often necessary to boost their immunogenicity with an adjuvant. This can also apply to some live, e.g. attenuated vaccines. An adjuvant is a substance that enhances the immune response to an antigen.

During work in the 1920s on the production of animal antiserum for human therapy, it was discovered that certain substances, notably aluminium salts added to antigens or emulsions incorporating antigen, greatly enhance antibody production, i.e. they act as adjuvants. Aluminium hydroxide is still widely used with, e.g. diphtheria and tetanus toxoid and insoluble tyrosine is used with some allergy vaccines. Other more soluble adjuvants also have desirable effects such as inducing a heightened immune response or driving the response towards for example a TH1 type response.

3 De-O-acylated monophosphoryl lipid A is known from GB-A-2220211 (Ribi). Chemically it can be a mixture of 3 de-O-acylated monophosphoryl lipid A with 4, 5 or 6 acylated chains and is now manufactured by Corixa Corporation. A preferred form of 3 de-O-acylated monophosphoryl lipid A (also referred to herein as MPL® adjuvant) is disclosed in International Patent Application No. WO92/16556.

International Patent Publication No. WO98/44947 described a formulation for use in desensitisation therapy of allergy sufferers which comprised an optionally modified allergen, tyrosine and 3 de-O-acylated monophosphoryl lipid A.

Considerable efforts have been made to produce better adjuvants, particularly for T-cell-mediated responses, but it should be stressed that few of these more recent adjuvants are yet accepted for routine human use. MPL® adjuvant, however, has been licensed for use with a Melanoma vaccine and allergy vaccines containing MPL® adjuvant are available as 'Specials' in Germany, Italy and Spain.

WO00/50078 to Chiron describes a composition which includes bioadhesives in combination with adjuvants and antigens for mucosal delivery. However, it only demonstrates the production of an IgG immune response with the composition. Further, the bioadhesive is an agent which physically or chemically binds to mucus. It is believed that there may be safety concerns associated with such bioadhesion of some antigen-containing compositions. Sublingual delivery is not taught; the test composition being administered intranasally.

Clearly there is still a need for a composition that generates a mucosal and systemic inrune response to protect against bacteria, viruses and other parasitic organisms, and that may be used as an allergy vaccine. Ideally such a composition should be administerable via a route which is associated with good patient compliance, such as the sublingual route. It has also been found that sublingual delivery may give rapid absorption and good bioavailability of the substance being delivered. Sublingual delivery may also be advantageous over intermittent injections in maintaining adequate blood concentrations of the substance being delivered. Preferably the composition should make use of conveniently available adjuvants.

SUMMARY OF THE INVENTION

The present invention relates to a sublingual delivery system and has advantages associated with this means of delivery. In more detail, we have now found it possible to use glycolipid adjuvants, such as MPL® adjuvant, with an antigen to produce a mucosal immune response (MIR) when administered sublingually. We understand we are the first to realise that the use of glycolipid adjuvants sublingually can produce a systemic IgG as well as a mucosal IgA-mediated response. Surprisingly we have also found that the MIR may be generated at a site which is distal to, as well as local to, the sublingual site of delivery. For example, IgA may be detected at other lymphoid tissues, such as in the intestinal tract, respiratory tract and genitourinary tract. This has particularly important implications for the treatment of, for example, sexually transmitted diseases, as sublingual application is convenient and may therefore lead to good patient compliance with any dosage regimen.

It appears that the effect of adjuvants is due mainly to two activities: the persistent concentration of antigen in a site where lymphocytes or other competent cells are exposed to it (the "depot" effect) and the induction of cytokines, which regulate lymphocyte function. Newer devices such as liposomes and immune-stimulating complexes (ISCOMS) may achieve the same purpose by ensuring that antigens trapped in them are delivered to antigen-presenting cells. Bacterial products such as mycobacterial cell walls, endotoxin etc. are believed to act by stimulating the formation of cytokines. Cytolcine induction may be particularly useful in immuno-compromised patients, who often fail to respond to normal vaccines. It is hoped that such cytokine induction might also be useful in directing the immune response in the desired direction, e.g. in diseases where only TH1 or TH2 cell responsiveness is wanted (Roitt et al "Immunology" 4th edition).

We also provide an antigen formulation, which can tilt the TH1-TH2 balance in favour of a TH1 response, which can be administered to the mucosae preferably to the mouth and in particular to the sublingual site. The formulation is useful in immunotherapy, particularly in the field of vaccines. It is also useful in studying immune responses and in the production of antibodies.

STATEMENT OF INVENTION

In its broadest sense the present invention relates to the finding that glycolipids will drive a systemic and mucosal humoral response to antigen when a composition containing them is administered sublingually in a human or animal. We have found that any convenient sublingually administerable excipient may be employed. The ability of a glycolipid adjuvant to drive serum IgG, $IgG_1$ and $IgG_{2a}$ when administered with antigen sublingually shows that the invention is applicable to prophylactic vaccines as well as allergy desensitisation. The ability of a glycolipid adjuvant to drive mucosal IgA after sublingual dosing additionally shows that the invention is a useful way to generate mucosal immunity. The generation of mucosal immunity is useful in protecting against airborne pathogens and sexually transmitted diseases in particular.

In general terms the present invention relates to a composition comprising (A) at least one antigen and (B) a glycolipid adjuvant and uses thereof.

In particular, according to one aspect of the present invention there is provided a method of producing a mucosal and/or systemic immune response in a human or animal in need of the same comprising administering a composition comprising at least one antigen and a glycolipid adjuvant.

Put another way the present invention relates to the use of at least one antigen and a glycolipid adjuvant in the preparation of a medicament for producing a mucosal and/or systemic immune response.

According to another aspect of the present invention there is provided a method of treating a mucosally transmitted disease comprising administering sublingually to a human or animal a composition comprising at least one antigen and a glycolipid adjuvant.

Put another way the present invention relates to the use of at least one antigen and a glycolipid adjuvant in the preparation of a sublingually-administerable medicament for treating a mucosally transmitted disease.

These methods of the present invention generate an IgA-mediated immune response.

Thus, the present invention also provides a method of producing an IgA immune response in a human or animal comprising administering sublingually a composition comprising at least one antigen and a glycolipid adjuvant.

Put another way the present invention relates to the use of at least one antigen and a glycolipid adjuvant in the preparation of a sublingually-administerable medicament for producing an IgA immune response.

The composition should be administered in an effective amount. The term "effective amount" refers to a non-toxic but sufficient amount of the composition to provide the desired immunological response. An appropriate effective amount may be determined by one skilled in the art.

The compositions according to the invention may be either prophylactic (i.e. prevent infection) or therapeutic (to treat disease after infection).

Preferably the composition is administered to humans, mammals and other primates, including non-human primates such as apes and monkeys, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The method of the present invention may also generate an IgG-mediated immune response.

According to another aspect of the present invention there is provided a composition comprising:
(A) one or more antigens; and
(B) a glycolipid adjuvant.

In an especially preferred embodiment the glycolipid is a TH1-inducing adjuvant.

Preferably the composition useful in the present invention comprises a sublingually administerable diluent, excipient or carrier which aids availability of (A) and (B) at the site of administration (mucosal sublingual site).

Preferably the antigen is derived from a bacterium, virus, prion, neoplasm, autoantigen, plant, animal, or other pathogenic or non-pathogenic organism, synthetic or recombinant material.

The antigen may comprise selected portions of antigenic molecules, or molecules made by synthetic or recombinant technologies.

Preferably, the antigen is an allergen. Allergens are types of antigens, which have the propensity to induce allergy. The allergen may comprise selected portions of allergenic molecules, or molecules made by synthetic or recombinant technologies.

Hereafter the words antigen or antigens encompass the word allergen or allergens respectively.

Preferably the antigen is in the form of a polypeptide, carbohydrate or lipid. Alternatively, the antigen may be in the form of a vector comprising a polynucleotide encoding an antigenic polypeptide, and where said polynucleotide is operably linked to a regulatory sequence which regulates expression of said polynucleotide.

Preferably the TH1-inducing adjuvant is but is not limited to MPL® adjuvant, 3D-MPL or a derivative or salt thereof, or is some other TH1-inducing adjuvant or combinations of such adjuvants.

Preferably the composition is in the form of a vaccine.

Preferably the composition is in the form of an aqueous solution, a gel, a patch, a lozenge, capsule or a tablet, most preferably an aqueous or gel solution.

The present invention also provides for use of the composition in the preparation of a medicine for treatment of or prevention of a bacterial, viral prion infection, or other disease such as cancer, autoimmuruity or allergy in a human or animal.

The invention further provides for use of the composition in a method for producing one or more antibodies that recognise said antigen. The antibodies produced may be used in the manufacture of a medicament for treating bacterial or viral infection, cancer, autoimmunity or allergy in a human or animal. The present invention is particularly important in relation to airborne pathogens and sexually transmitted diseases.

The present invention further provides a method for preparing an antiserum or immunoglobulin preparation from it, comprising immunising a human or animal with a composition of the present invention.

The present invention also provides a method for preparing a composition of the present invention comprising mixing a solution of antigens and the glycolipid adjuvant with a pharmaceutically acceptable diluent, carrier or excipient, preferably an aqueous solution or a gel.

DETAILED DESCRIPTION

Various further preferred features and embodiments of the present invention will now be described by way of non-limiting example.
Immune Response An immune response is a selective response mounted by the immune system of vertebrates in which specific antibodies and/or cytotoxic cells are produced against invading microorganisms, parasites, transplanted tissue and many other substances which are recognised as foreign by the body, i.e. antigens. The production of antibodies circulating in the blood is known as a humoral response; the production of cytotoxic cells as a cell-mediated or cellular immune response.

The cells involved in the immune system are organised into tissues and organs in order to perform their functions most effectively. These structures are collectively referred to as the lymphoid system. The lymphoid system comprises lymphocytes, accessory cells (macrophages and antigen-presenting cells) and in some cases, epithelial cells. It is arranged into either discretely capsulated organs or accumulations of diffuse lymphoid tissue. The major lymphoid organs and tissues are classified as either primary (central) or second (peripheral). The present invention focuses on the secondary lymphoid organs. Secondary lymphoid organs include mucosa-associated tissues, and provide an environment in which lymphocytes can interact with each other, with accessory cells, and with antigens. In more detail, the generation of lymphocytes in primary lymphoid organs (lymphopoiesis) is followed by their migration into peripheral secondary tissues. The secondary tymphoid tissues comprise well-organised encapsulated organs—the spleen and lymph node—and non-encapsulated accumulations that are found around the body. The bulk of the non-organised lymphoid tissue is found in associated with mucosal surfaces and is called mucosa-associated lymphoid tissue (MALT).

The muscosal system protects the organism from antigens entering the body directly through mucosal epithelial surfaces. Thus, lymphoid tissues are found associated with surfaces linig the intestinal tract, the respiratory tract and genitourinary tract. The present invention particularly relates to lymphoid tissues found associated with surfaces lining the sublingual region. The major effector mechanism at these sites is secretory IgA (sIgA), secreted directly onto the mucosal epithelial surfaces or the tract.

Secretory IgA represents over 95% of all Ig found in secretions and is primarily dimeric with two monomeric units covalently joined by a J chain. Dimeric IgA binds to a polymeric immunoglobin receptor pIGR on the basal surface of mucosal epithelial cells. This IgA-pIGR complex is endocytosed and transported to the apical (luminal) surface of the epithelial cell. During this transport process, a small piece of the pIGR is cleaved with the remaining component now called the secretory component. Thus, IgA is secreted as dimeric IgA bound to a secretory component.

Secretory IgA does not activate the complement system but coats bacteria and viruses such as polio, coxsacltie, rota and herpes, thus preventing their adherence to mucosal lining epithelium. Also, some viruses within surface epithelia can be neutralised by pIGR-internalised IgA.

The generation of secretory IgA, and hence the generation of a mucosal immune response (hereinafter MIR), may be detected using techniques standard in the art, such as ELISA. By way of example only the standardised ovalbumin ELISA test used in Examples 1 and 2 is described in Preparation Example 1.

A MIR to an antigen may lead to a state of systemic response to the same antigen, known as mucosal or oral tolerance. Thus, mucosal immunisation is an effective way to stimulate both local and systemic immune responses.
Antigen Historically, in the art, the term "antigen" was used for any molecule that induced B cells to produce a specific antibody. Now, however, the term may be used to indicate any molecule that can be specifically recognised by the adaptive elements of the immune response, i.e. by B cells or T cells, or both. Thus the term "antigen" is understood in the art to mean a molecule which reacts with preformed antibody and/or with various specific receptors on T and B cells. This definition includes what are traditionally known as "allergens", i,e, an agent, e.g. pollen dust, that causes IgE-mediated hypersensitivity.

An allergy (type 1 hypersensitivity) is a response to environmental antigen (allergen) in which IgE antibody is produced in relatively large amounts in allergic subjects compared with a non allergic person and is attached to mast cells and basophils in particular. An immediate hypersensitivity reaction is produced by mast cell products (histamine, etc.) when they are released following the reaction between IgE on the mast cell or basophil surface and allergen causing asthma, hay fever, serum sickness, systematic anaphylaxis or contact dermatitis. There are four types of hypersensitivity reaction (Types I, II, III and IV). The Type 11 and 111 are antibody-mediated; the fourth is mediated mainly by T cells and macrophages. The invention allows one to inmiunise with an allergen in order to bias away from an allergic IgE immune response towards a non-allergic immune response.

Thus, the "antigen" used in the present invention may be an "allergen" derived from any allergy causing substance, such as pollen (e.g. ragweed or birch pollen), food, insect venom, mould, animal fur or house dust mite (*D. farinae* or *D. pteronyssinus*).

The antigen used in the present invention is preferably an immunogen, i.e. an antigen that activates immune cells to generate an immune response against itself.

In a preferred embodiment, the present invention relates to a formulation for use as a vaccine and the antigen is one useful in such a vaccine.

The antigen used in the present invention can be any appropriate antigen, which is or becomes available.

The type of antigen used in a vaccine depends on many factors. In general, the more antigens of a microbe retained in the vaccine the better and living organisms tend to be more effective than killed ones. Exceptions to this rule are diseases where a toxin is responsible for any pathogenic effect. In this case the vaccine can be based on the toxin or toxoid alone.

The antigen used in the present invention may be derived from any living organisms; intact or non-living organisms; subcellular fragments; toxoids; recombinant DNA-based antigens or anti-idiotypes or synthetic antigens. The antigen may be derived from natural or attenuated organisms, which may be viral or bacterial. The type of antigen may be a capsular polysaccharide, surface or internal antigen. If recombinant DNA-based, the antigen may be obtained from a cloned and expressed gene or naked DNA.

The antigen may be modified by reaction for example with a cross-linking agent, such as a dialdehyde, more particularly glutaraldehyde.

For example micro-organisms against which vaccines are available or are sought include Salmonella, Shigella, Klebsiella, Enterobacter, Serratia, Proteus, Yersinia, Vibrio, Aeromonas, Pasteurella, Pseudomonas, Acinetobacter, Moraxella, Flavobacterium, Bordetella, Actinobacillus, Neisseria, Brucella, Haemophilus and *Escherichia coli*.

Preferred vaccines include vaccinia (for smallpox); vole bacillus (for TB); polio; measles, mumps; rubella; yellow fever; varicella-zoster; BCG; rabies; influenza; hepatitis A; typhus; pertussis; typhoid; cholera; plague; penumoccoccus; meningococcus; *Haemophilus influensae*; hepatitis B; hepatitis C; tetanus and diphtheria. Toxin based vaccines include *Clostridium tetani, Corynebacterium diphtheriae, Vibrio cholerae* and *Clostridium perfringens*.

Other major diseases for which vaccines may be useful include: HIV, herpes, viruses, adenoviruses, rhinoviruses, staphytococci, group A streptococci, *Mycobacterium leprae, Treponema pallidum*, Chiamydia, Candida, Pneumocystis, malaria, trypanosomiasis; Chagas' disease; schistosomiasis and onchoceriasis.

Sexually transmitted diseases for which vaccines may be useful include, in addition to HIV and herpes mentioned above: *Neisseria gonorrhoeae, Treponema pallidum, Trichomonas vaginalis, Haemophilus ducreyi*, Chaamydia, *Calymmatobacterium granulomatis*_and hepatitis.

The presence of tumour antigens also has been demonstrated, and, as a result, the concept of vaccinating against cancer has arisen. Also, in principle, conception and implantation can be interrupted by inducing immunity against a wide range of pregnancy and other reproductive hormones.

Typically, the antigen will be a polypeptide, but alternative antigenic structures, such as nucleic acid, carbohydrates, lipids, whole or attentuated organisms, such as viruses, bacteria or protozoa may also be used.

The term "polypeptide" is used generally to denote molecules constructed of a plurality of amino acids, the amino acids being joined together covalently such as through peptide bonds. Generally, polypeptide is used interchangeably with "protein" or "peptide" in that no difference in size or function is implied. Recombinant polypeptides may be prepared by processes well known in the art such as those described in Sambrook et al, "Molecular Cloning: A Laboratory Manual"; $2^{nd}$ Ed., Cold Spring Harbor Lab. Press (1989).

Glycolipid Adjuvant

In general terms an adjuvant is a substance that non-specifically enhances the immune response to an antigen, i.e. is an immunostimulant. In general terms a glycolipid is a cell membrane lipid molecule with a carbohydrate chain attached to a hydrophobic tail. The preferred glycolipid adjuvants of the present invention are modified lipopolysaccharides. The lipopolysaccharide is modified such that its toxicity is reduced compared to the corresponding wild type lipopolysaccharide or lipopolysaccharide from which it has been derived. Preferably the glycolipid adjuvant used in the present invention is a detoxified enterobacterial lipopolysaccharide or its lipid A component. The term "detoxified" refers to both completely nontoxic and low residual toxic mutants of the toxin. Preferably, the detoxified adjuvant retains a toxicity of less than 0.01%, more preferably 0.001%, of the corresponding wild type toxin. Toxicity may be measured in CHO cells by evaluation of morphological changes.

Preferably the glycolipid adjuvant is a TH1-inducing adjuvant. By "TH1-inducing adjuvant" we mean an adjuvant, having properties that enhance the TH1 response to an antigen. However, such an adjuvant may also have the propensity to simply increase the level of antibody or antigen specific cells produced or even, by the induction of modulating cytokines cause anergy (non-responsiveness) in certain cell populations.

In more detail, the immune response to antigen is generally either T cell mediated (which may involve cell killing) or hunoral (antibody production via recognition of epitopes on the antigen). The pattern of cytokine production by T cells involved in an immune response can influence which of these response types predominates: for example cell mediated immunity (TH1) is characterised by high IL-2 and IFNγ but low IL-4 production, whereas in hunoral immunity (TH2) the pattern can be low IL-2 and IFNγ but high IL-4, IL13, IL-5. Responses are usually modulated at the level of the secondary lymphoid organ or cells, so pharmacological manipulation of specific T cell and antigen presenting cell cytokine patterns can influence the type and extent of the immune response generated.

The TH1-TH2 balance refers to the interconversion or predominance of the two different forms of helper T cells. The two forms have large scale and often opposing effects on the immune system. If an immune response favours TH1 cells, then these cells will drive a cellular response with associated antibody production, whereas TH2 cells will drive an antibody-dominated response. The isotype of antibodies responsible for some allergic reactions, IgE, and associated inflammatory responses are induced by cytokines from TH2 cells.

The effectiveness of an adjuvant as a THI-inducing adjuvant may be determined by determining the profile of antibodies directed against an antigen resulting from administration of this antigen in vaccines, which are also comprised of the various adjuvants.

Preferably the adjuvant is a modified hipopolysaccharide. As described in U.S. Pat. No. 4,912,094 enterobacterial lipopolysaccharides (LPS) is a powerful immunostimulant. However, it can also illicit harmful and sometimes fatal responses. It is now known that the endotoxic activities associated with LPS result from its lipid A component. Accordingly the present invention more preferably uses a detoxified derivative of lipid A. Corixa Corporation produced a derivative of lipid A originally known as refined detoxified endotoxin (RDE) but which has become known as monophosphoryl lipid A (MPL® adjuvant). MPL® adjuvant can be produced by refluxing LPS or lipid A obtained from heptoseless mutants of gram negative bacteria (e.g. Salmonella sp.) in mineral acid solutions of moderate strength (e.g. 0.1N HCl) for a period of around 30 minutes. This treatment results in loss of the phosphate moiety at position 1 of the reducing-end glucosamine. In addition the core carbohydrate can be removed from the 6' position of the non-reducing glucosamine during this treatment. MPL® adjuvant and 3-deacylated monophosphoryl lipid A and methods for their manufacture are disclosed in U.S. Pat. Nos. 4,436,727, and 4,912,094 and reexamination certificate B1 U.S. Pat. No. 4,912,094.

Preferably, however, a modified LPS or lipid A is used in which the detoxified lipid A retains the core moiety attached to the 6' position of non-reducing glucosamine. Such derivatives of LPS and lipid A are also described in U.S. Pat. No. 4,912,094. In more detail, U.S. Pat. No. 4,912,094 discloses a modified lipopolysaccharide which is obtained by the method of selectively removing only the β-hydroxymyristic acyl residue of lipopolysaccharide that is ester-linked to the reducing-end glucosamine at position 3' of said lipopolysaccharide, which comprises subjecting said lipopolysaccharide to alkaline hydrolysis. Such de-O-acylated monophosphoryl lipid A (MPL® adjuvant), diphosphoryl lipid A (DPL) and LPS may be used in the present invention. Thus in a preferred embodiment, the present invention uses MPL® adjuvant, DPL or LPS in which the position 3' of the reducing end glucosamine is de-O-acylated. These compounds are known as 3D-MPL, 3D-DPL and 3D-LPS respectively.

In U.S. Pat. No. 4,987,237 derivatives of MPL® adjuvant having the formula:

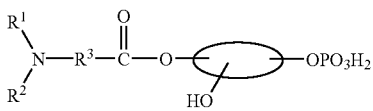

are described, and wherein $R^1$ and $R^2$ are H, $R^3$ is straight or branched chain hydrocarbon composed of C, H and optionally O, N and S, which if more than one atom may be the same or different, wherein the total number of C atoms does not exceed 60, and the circle represents an MPL nucleus.

Alternatively the MPL® adjuvant derivative has the formula

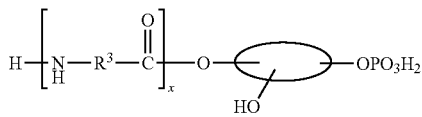

wherein the segment of the derivative represented by

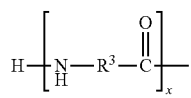

contains 2-60 C atoms and wherein $R^3$ is straight or branched chain hydrocarbon composed of C, H and optionally O, N and S, which if more than one atom may be the same or different, and x is a minimuim of 1 and can be any whole number such that the total number of C atoms in all x segments does not exceed 60, and wherein the chemical structure of each $R^3$ may be the same or different in each such segment and wherein the circle represents an MPL nucleus.

One commercially available adjuvant from Corixa Corporation includes 2% Squalene, 0.2% Tween 80 and as well as the MPL® adjuvant Another commercially available adjuvant is Detox® adjuvant (Corixa Corporation) which comprises MPLO adjuvant and mycobacteria cell wall skeleton.

All such derivatives or salts of LPS or lipid A which are or become available may be used in the present invention. Preferably derivatives and salts are ones which are pharmaceutically acceptable.

The TH1-inducing adjuvant can be mixed with the other components of the composition immediately prior to administration. Alternatively it can be formulated together with the other components during manufacture of the product. Alternatively, it can be administered at a different time than the other components. Administration can be by a number of routes. Preferably the glycolipid adjuvant is administered in an amount from 1.0 mg to 250 mg, more preferably 25 mg to 50 mg.

Vaccines

One aspect of the present invention relates to a method for inducing an immunological response, preferably a mucosal immunological response, in a mammal, preferably humans, which comprises sublingually inoculating an individual with the composition of the present invention to produce antibody, preferably IgA, and/or a T cell immune response. Preferably the response is adequate to protect said individual from infection, particularly bacterial or viral infection. Preferably the response is adequate to protect said individual from disease, whether that disease is already established within the individual or not. Thus, the immunological response may be used therapeutically or prophylatically.

Vaccines may be prepared from the composition of the present invention. The preparation of vaccines containing an antigen as the active ingredient is known to one skilled in the art. Typically, such vaccines are prepared either as liquid solutions or suspensions; solid forms suitable for solution in, or suspension in, liquid prior to administration may also be prepared. The preparation may also be in a gel, emulsified, or the composition encapsulated in liposomes. Suitable excipients are, for example, water, ammonium phosphate, dextrose, glycerol, ethanol, or the like and combinations thereof.

Compositions include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to adminnistration, e.g. as a suspension. Reconstitution is preferably effected in buffer.

In addition, if desired, the vaccine may contain minor amounts of auxiliary substances such as wetting or emulsifying agents, pH buffering agents and/or further adjuvants, which enhance the effectiveness of the vaccine.

The proportion of antigen and adjuvant can be varied over a broad range so long as both are present in effective amounts. Typically, the vaccines are formulated to contain a final concentration of antigen in the range of 0.2 µg/ml to 200 µg/ml, preferably 5 µg/ml to 50 µg/ml, most preferably about 15 µg/ml. The preferred formulation can be determined through known dose range protocol and reference is made to "Remington: The Science and Practice of Pharmacy", Mack Publishing Company, 19th Edn, 1995.

After formulation, the vaccine may be incorporated into a container which can be sterile that may then be sealed and stored at low temperature, for example 4° C., or it may be freeze-dried. Lyophilisation permits long-term storage in a stabilised form.

The antigens used in the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trinmethylamine, 2-ethylamino ethanol, histidine and procaine.

The composition be presented as a tablet, capsule or other convenient formulation with the excipients required to make such a formulation.

Preparation of Antibodies Using the Composition of the Invention

Compositions according to the invention may be used directly as immunogens by the routes of administration described herein, without the use of further adjuvants to generate antisera, specific immunoglobulins or monoclonal antibodies. The invention thus provides a method for inducing antigen specific immunoglobulin production comprising the steps of:

a) Immunising an animal with a composition according to the present invention; and
b) recovering immunoglobulin specific for a region of the antigen of the composition from the serum of the animal.
c) Selecting monoclonal antibody producing clones of cells.

Techniques for generating antibodies are taught in Kohler and Milstein, Nature (1975) 256:495-497.

The animals used for antibody production may be any animals normally employed for the purpose, particularly mammals. Especially indicated are mice, rats, guinea pigs and rabbits. The animals will be treated with the formulations described herein.

More particularly, the formulation of the present invention comprising the antigen can be used to produce antibodies, both polyclonal and monoclonal. If polyclonal antibodies are desired, a selected mammal (e.g., mouse, rabbit, goat, horse, etc.) is immunised. Serum from the immunised animal is collected and treated according to known procedures. If serum contains polyclonal antibodies to other antigens, the required polyclonal antibodies can be purified by immunoaffinity chromatography. Techniques for producing and processing polyclonal antisera are known in the art.

Monoclonal antibodies directed against antigens used in the invention can also be readily produced by one skilled in the art. The general methodology for making monoclonal antibodies by hybridomas is well known. Immortal antibody-producing cell lines can be created by cell fusion, and also by other techniques such as direct transformation of B-lymphocytes with oncogenic DNA, or transfection with Epstein-Barr virus. Panels of monoclonal antibodies produced against antigens can be screened for various properties; i.e., for isotype and epitope affinity.

An alternative technique involves screening phage display libraries where, for example the phage express scFv fragments on the surface of their coat with a large variety of complementary determining regions (CDRs). This technique is well known in the art.

Antibodies, both monoclonal and polyclonal, which are directed against antigens are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment, as well as for an elucidation of the inmmunogenic regions of antigens.

For the purposes of this invention, the term "antibody", unless specified to the contrary, includes fragments of whole antibodies that retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Preparation of Composition

The composition of the present invention may be prepared by mixing an aqueous solution of the antigen with the glycolipid adjuvant, and adding the mucosally administerable diluent, excipient or carrier either before or after the aforementioned mixture. Alternatively the glycolipid adjuvant may be co-precipitated with the antigen. As well as being mixed or co-precipitated with the other components of the composition prior to administration, the glycolipid adjuvant can be administered at a different site and/or time to the other components. The mixture of glycolipid adjuvant and antigen can also be incorporated in gels, capsules, lozenges etc. or can also be presented in various devices such patches which can be bi- or preferably uni-directional.

MPL (or other TH1-inducing adjuvant) which has been dissolved by sonification or other means (described later in Preparation of a solution of MPL® adjuvant), can be diluted by various means prior to its addition to antigens. The preparation of MPL is initially made at a concentration of typically between 0.5 mg per ml and 4 mg per ml, for example 1 mg per ml. It can then be diluted to a concentration of between 500 µg/ml and 20 µg/ml, preferably 100 µg/ml. This dilution can be made in pure water or in other solvents such as in an aqueous glycerol solution containing between 1% and 50% glycerol.

Suitable physiologically acceptable carriers and diluents include sterile water or 5% dextrose water solution. The compositions are for human or veterinary use and are formulated for mucosal, preferably sublingual delivery.

The routes of administration and dosages described herein are intended only as a guide since a skilled practitioner will be able to determine readily the optimum mucosal route of administration and dosage for any particular patient and condition.

Formulation, Dosage and Administration of Compositions

The composition of the present invention may conveniently be formulated with a pharmaceutically acceptable diluent, carrier or excipient suitable for sublingual administration. Details of pharmaceutical excipients may be found in "Handbook of Pharmaceutical Excipients", $2^{nd}$ Ed. (1994), The Pharmaceutical Press, London, Editors: Wade & Weller.

We have found that an important aspect of the present invention is sublingual administration of the composition of the present invention. A gel or other viscous formulation may be expected to be preferred due to increased antigen contact with the sublingual surface. However, results may also be achieved with other formulations such as an aqueous solution. In mice, a simple solution was found to give similar results to a gel formulation. It is not required nor desirable that the formulation should physically or chemically bind to the mucosal tissue.

Formulations suitable for sublingual administration include aqueous and non-aqueous sterile solutions which may contain anti-oxidants, buffers, bacteristatic compounds and solutes which render the formulation isotonic with the bodily fluid, preferably the mucus, of the individual; the aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

Preferably a carrier is also present in the composition according to the invention. The carrier may be an oil in water emulsion, or an aluminium salt, such as aluminiumn phosphate or aluminium hydroxide.

Non-toxic oil in water emulsions preferably contain a non-toxic oil, e.g., squalane or squalene, an emulsifier, e.g. Tween 80, in an aqueous carrier. The aqueous carrier may be, for example, phosphate buffered saline.

The present invention also provides a polyvalent vaccine composition comprising a vaccine formulation of the invention in combination with other antigens, in particular antigens useful for treating cancers autoimmune diseases and related conditions.

In general, carriers may include, but are not limited to, dextrose, water, glycerol, ethanol and combinations thereof.

The invention further relates to pharmaceutical packs and kits comprising one or more containers filled with one or more of the ingredients of the aforementioned compositions of the invention.

Administration of these compositions may be in the form of salves, pastes, gels, solutions, powders and the like. Gels may conveniently be formulated using carbopol also known as carbomer—a carboxyvinyl polymer, or a cellulose-based thickening agent such as hydroxyethyl cellulose, hydroxypropyl cellulose or hydroxypropyl methylcellulose, carboxymethylcellulose calcium, carboxymethylcellulose sodium, ethyl cellulose, methylcellulose. Gels may also be conveniently formulated using: acacia, alginic acid, bentonite, cetostearyl alcohol, gelatin, guar gum, magnesium aluminium silicate, maltodextrin, polyvinyl alcohol, propylene carbonate, propylene glycol alginate, colloidal silicon dioxide, sodium alginate, tragacanth, and/or xanthan gum. Particularly preferred are carbopol and the cellulose-based agents.

The compositions are administered in a manner compatible with the dosage formulation, and in such amount as will be prophylactically and/or therapeutically effective. The quantity to be administered, which is generally in the range of 0.5 μg to 250 μg of antigen per dose, depends on the subject to be treated, the capacity of the subject's immune system to synthesise antibodies, and the degree of protection desired. A preferable range is from about 2 μg to about 40 μg per dose. In some cases the patient will be treated with a series of administrations which will include a rising antigen dose regime.

A suitable dose size is about 0.1 ml, but within a regime this does may start at a lower volume and finish at a higher volume. The precise amounts of active ingredient administered may depend on the judgement of the practitioner and may be peculiar to each individual subject.

The composition may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1 to 4 months for a second dose, and if needed, a subsequent dose(s) after several months. When the product is being used for the treatment of allergy the administration regimes will include more frequent dosing. The dosage regimen will also, at least in part, be determined by the needs of the individual and be dependent upon the judgement of the practitioner.

In addition, the composition containing the antigen(s) may be administered in conjunction with other immunoregulatory agents, for example, immunoglobulins.

The invention will be described with reference to the following examples that are intended to be illustrative only and not limiting.

EXAMPLES

Preparation of a Solution of MPL® Adjuvant

A 4 mg/ml solution of 1,2-dipalmitoyl-SN-glycero-3-phospho choline (DPPC) in absolute ethanol was prepared. For each 1.0 mg of NIPL-TEA (triethylanuine) salt to be solubilised, 27 μl of DPPC were added to dissolve the MPL. MPL may be prepared as described above. The ethanol was removed by blowing a stream of $N_2$ gently into the vial. Next 1.0 ml of pyrogen-free water for injection was added for each mg of MPL in the dried MPL/DPPC mixture. The solution was sonicated in a bath sonicator at 60-70° C. until clear. The MPL/DPPC solution was then filter sterilised by filtration through a SFCA 290-4520 Nalgene 0.2 μm filter. The MPL/DPPC solution was aseptically dispensed at 1.0 mg/ml into depyrogenated vials, labelled MPL-AF (MPL solubilised in the surfactant DPPC), and stored at 4° C.

Formulation of Ovalbumin (XOA)/MPL® Adjuvant/Sublingual Gel.

TH1 inducing activity in mice can be equated with the production of specific IgG2a and IgG2b antibodies and the TH2 inducing activity with the production of specific IgG1 antibodies and IgE antibodies. Specific secretory IgA antibodies can identify whether a mucosal response has occurred whether it be local (salivary antibody) or distal (vaginal antibody) following sublingual immunisation. The immunogenic potential of a formulation can be investigated, however, by measuring solely the specific IgG response in serum.

Therefore, as an example, an experiment was carried out in mice to demonstrate the profiles of the allergen specific antibodies to an exemplar; ovalbumen (XOA) which is accepted as a model antigen and is also a well-known allergen derived from chicken eggs.

| | Stock Materials. | |
|---|---|---|
| 1. | Carbopol TR-1 NF stock (0.83%) | |
| | A. 100 mg carbopol TR-1 NF in 20 ml WFI (water for injection) = 0.9% w/v gel. | |
| | B. To A was added 0.8 ml 10% v/v TEOA (triethanolamine) = 0.8% w/v gel. | |
| 11 | MPL AF glycerol (20 mg/ml) | |
| | A. MPL | 40 mg |
| | DPPC | 4.32 mg |
| | Glycerol | 800 μl |
| | WFI qs | 40 ml |
| | Sonicated to particle size approx. = 80 nm | |
| | B. Lyophilised | |
| | C. Reconstituted with 1.2 ml WFI-20 mg/ml MPL. | |
| 111 | Ovalbumin Stock (33 mg/ml) | |
| | Ovalbumin | 33 mg |
| | WFI | 1.0 ml |
| | Formulation For Injection | |
| | Carbopol stock | 1920 μl |
| | Ovalbumin stock | 480 μl |
| | Glycerol | 480 μl |
| | WFI | 720 μl |
| | MPL glycerol | 400 μl |
| 1. | Carbopol, XOA, glycerol and WFI were added into a 5 ml vial and mixed by vortexing. | |
| 2. | MPL glycerol was added to the above and further vortexing carried out. | |

Immunisation of Mice

Groups of 5 eight-week-old female Balb/C mice were anaesthetised with Ketamine. When the mice were unconscious, 20 μl of the appropriate gel containing various amounts of XOA was placed under the tongue for 5 minutes. The gels were rinsed out of the mouth after 5 minutes. With 1.0 ml 0.9% saline using a syringe and a gavage needle.

Three weeks later the mice were treated identically to the first treatment. The mice were bled 2 weeks after the second treatment and sera collected. These were assayed for XOA specific IgG antibodies using an ELISA assay.

Results

Anti-Ovalbumin IgG Responses in Mice Administered Either 83.2 μg or 3.4 μg Ovalbumnin and 33.6 μg MPL in 20 μl Carbopol Gel via the Sublingual Route, Boosted after 3 Weeks and Bled 2 Weeks later. (Average OD (optical density) Values of 5 Mice per Group).

OD Values at Different Serum Dilutions

|  | 1/10 | 1/30 | 1/90 | 1/270 | 1/610 |
|---|---|---|---|---|---|
| Group 1 Dose 83.2 μg XOA | 1.1 | 1.0 | 0.75 | 0.5 | 0.3 |
| Group 2 Dose 3.4 μg XOA | 0.6 | 0.5 | 0.35 | 0.15 | 0.05 |
| Group 3 Carbopol only | 0.15 | 0.1 | 0.05 | 0.05 | 0.05 |

Example 2

Preparation of Materials for Immunisation of Mice

The immunising doses of XOA/MPL in carbopol or alternatively in the diluent (aqueous formulation) without MPL were prepared as described in Example 1 except for the use of different doses.

Immunisation of Mice

1. Each mouse was anaesthetized before administration
2. 20 μl of the appropriate material was placed under the tongue for 5 minutes. Thus, each of the groups of mice was administered the following amounts of substances in 20 μl.

| Group | Antigen | MPL | Excipient |
|---|---|---|---|
| 1 | 80 μg ovalbumin | 20 μg MPL | Carbopol |
| 2 | 80 μg ovalbumin | 0 μg MPL | Carbopol |
| 3 | 0 μg ovalbumin | 160 μg MPL | Carbopol |
| 4 | 80 μg ovalbumin | 40 μg MPL | Diluent |

3. The material was rinsed out of the mouth after 5 minutes with 1.0 ml of 0.9% saline
4. Three weeks after the primary vaccination and again a further two weeks after this the mice were retreated
5. Mice were bled 2 weeks after the third application and the sera stored until use at −20 C. Nasal and pulmonary washings were made and stored under the same conditions.
6. Sera and washings were tested for ovalbumin specific antibodies as previously.

Results

Serum IgG antibodies specific for XOA Titre log(2)/reference titre $(\log)_2$ (SD)

| GROUP | Serum IgG1 | Serum IgG2a | Serum IgG |
|---|---|---|---|
| 1 | 0.625 (0.375) | 0.35 (0.4) | 0.6 (0.3) |
| 2 | 0 | 0 | 0.2 (0.05) |
| 3 | 0 | 0 | 0.25 (0.02) |
| 4 | 0.95 (0.01) | 0.85 (0.2) | 1.0 (0.05) |

Geometric Mean Anti XOA IgA Antibodies in Different Fluids (SD)

| GROUP | SERUM | NASAL WASH | PULMONARY WASH |
|---|---|---|---|
| 1 | 0 | 73.6 (154.2) | 238.5 (533.4) |
| 2 | 0 | 0 | 0 |
| 3 | 0 | 0 | 0 |
| 4 | 2,291.3 (2,577.1) | 568.5 (395.4) | 2,518.4 (3,403.1) |

The strong serum IgG response to XOA requires the addition of MPL, which also appears to have stimulated a TH1 type response indicated by the IgG2a antibody response.

A novel and unexpected finding was the strong induction of an XOA-specific IgA response when MPL was used as an adjuvant.

In mice there was no apparent advantage of using carbopol as an excipient. In fact there was strong evidence that the aqueous formulation of XOA and MPL was more immunogenic for both IgG and IgA induction without carbopol. This included serum IgA, only seen in the absence of carbopol. However, it is necessary to use excipients in the formulation of vaccines and carbopol may be a useful and convenient excipient formulation for human or animal use.

Preparation Example 1

Ovalbumin Elisa

1. Sera (diluted 1:2 in borate buffer) from each of the five mice in each group are tested in an ELISA assay to determine the anti-ovalbumin IgG or IgA antibody titers.
2. To run the ELISA, the following equipment and supplies are required:
   A. Immulon 2 plate, 96 well, flat bottomed, DYNATECH LABORATORIES catalog #011-010-3455. Three plates per product lot tested (enough to test sera from 10 mice in duplicate).
   B. Ovalbumin (chicken egg), Sigma Grade 5. Stock solution (1 mg/mL in Water for Injection) made fresh each time the assay is run
   C. Clean (autoclaved) pipet tips
   D. 20, 100, 200, 1000 μl pipettors
   E. 8 charnel pipettor; 200 μl size
   F. Clean (new) 13 mm test tubes or 2 mL cryovials and rack
   G. Parafilm or Saran Wrap
   H. 1N $H_2SO_4$
   I. Horse radish peroxidase-labeled anti-IgG or anti-IgA secondary antibody (Used at 1:5,000). Southern Biotechnology Associates, Inc.
   J. OPD kit: o-Phenylenediamine tablets, one per plate and diluent. Abbott Labs' in vitro Test No. 7181E. Often available in house.
   K. Mouse sera to be tested. Sera should have been diluted 1:2 in Borate Buffer for long-term storage.
   L. Borate Buffer (BB):
      Dissolve the following 14 L sterile WFI:
         12.4 g Boric Acid, Fisher Scientific #A73-500
         0.764 g Sodium Borate (Borax), Fisher Scientific 4S248-500
         17.53 g Sodium Chloride, Fisher Scientific #S271-500
      Store at room temperature, expires in six months
   M. Borate Buffer+0.1% Tween 20 (BB-T20):
      Add 1 mL Tween-20 (Sigma #P-1379) to 1 liter BB, mix thoroughly.
      Store at room temperature, expires in six months.
   N. Borate Buffer-Tween-20-1% BSA (BB-BSA):
      Dissolve 1.90 g EDTA (tetrasodium, Fisher Scientific #BP 121-500) and 10 g BSA (Fraction V, protease-free, Boehringer Mannheim #100-350) in 1 liter BB-T20.
   O. 0.05 M Carbonate/bicarbonate buffer solution:
      Dissolve 4.2 g of $NaHCO_3$ and 5.3 g of $Na_2CO_3$ in 1 liter of RO water or sterile Water for Irrigation and adjust the pH to 9.6. Store at 4° C., expires in three months. Warm to room temperature before use.

P. Automatic pipettor
Q. Vortex mixer
R. Microcentrifuge racks
S. Plate reader, capable of taking O.D. readings at 490 nm
T. Incubator set at 37° C.
U. 25 mL serological pipettes (Fisher Scientific)
V. 15 mL polypropylene conical tubes (Fisher Scientific)
W. Reagent basins for multichannel pipettor
X. Automatic plate washer 3. Procedure for running the ELISA
A. Binding of the Test Antigen
   I. Antigen concentration for binding plates used in the adjuvant assay is 50 µg/ml:
      2.5 mL of the stock 1 mg/mL ovalbumin solution is added to 47.5 mL of 0.05 M carbonate/bicarbonate solution. This amount is enough to coat four 96 well plates at 100 µl per well.
   II. Plate is then covered with Saran Wrap and left level and undisturbed at 4° C. in the dark overnight.
B. Serum Dilutions: Briefly vortex each serum sample prior to dilution and each diluted sample prior to addition to the plate. A new pipet tip should be used to remove serum from the stock tubes when making the dilutions.
   I. The starting dilution for sera obtained from mice immunized with adjuvant and ovalbumin is 1:6.
C. Blocking the Plate
   I. When all sera samples are diluted, prepare the plate by vigorously shaking the coating buffer into a sink.
   II. Rap the plate sharply on a paper towel pad to remove excess solution. Wash the plate three times with BB-T20 wash solution using the automatic plate washer programmed to wash with 350 µL and to wait 5 seconds between each wash.
   III. Using the multichannel pipettor, add 250 µL BB-BSA per well. Cover and seal with saran wrap and incubate at 37° C. for 30 minutes.
D. Loading the Plate
   I. Vigorously shake the blocking buffer into a sink and rap the plate sharply on a paper towel pad to remove excess solution.
   II. Add 100 µl BB-BSA to all wells on each plate. Add 100 µl of the appropriately diluted serum samples to the appropriate wells in column #1. Each serum sample should be tested in duplicate.
   III. Using the multichannel pipettor, pipet 100 µl up and down eight times in column #1 to mix the sample, and then transfer 100 µl to column #2. Again, pipet up and down eight times to mix and transfer 100 µl to column #3. Repeat the serial dilutions through column #12. Discard the 100 µl in the tips after column 12 is mixed. There should now be 100 µl in each well of the plate.
E. Incubation
   Cover and seal the plates with Saran Wrap or Parafilm. Incubate the plates for 1 hour at 37° C. Remove the unbound antibody by the procedure outlined in step 3a, again washing the plate three times with BB-T20.
F. Conjugate
   I. Prepare the peroxidase-labeled anti IgG secondary antibody conjugate by diluting it 1:5,000 in BB-BSA (10 µl antibody in 50 mL BB-BSA in a 50 mL conical tube). Invert the tube >20 times and vortex for 30 seconds to thoroughly mix. Pour the diluted antibody into a clean reagent basin. Anti IgA conjugate may be prepared in a corresponding manner.
   II. Add 100 µl of conjugate solution to each well of the plate, including blank wells.
   III. Cover and incubate plate for 1 hour at 37° C.
   IV. Remove the conjugate solution and wash plate three times as in step 3a.
G. Color Developing:
   I. Prepare the substrate/colorimetric reagent 10-15 minutes prior to use (to give it time to dissolve completely) by dissolving 3 optical density developing tablets in 30.4 mL Substrate Buffer in a foil-covered 50 mL polypropylene conical tube.
   II. Using the multichannel pipettor, add 100 µl of reagent to each well. Incubate at room temperature for 15 minutes.
   III. Stop the reaction after 15 minutes by adding 50 µl of IM sulfuric acid to each well with the multichannel pipettor.
H. Reading the Plate
   I. The plates should be "stopped" in a sequential fashion, with 1-2 minutes between each plate, so that the time from "stop" to "read" is consistent between plates (after stopping the reaction on the last plate, read the first plate on the appropriate plate reader at 490 nm. Read the second plate 1-2 minutes later, and the third plate 1-2 minutes after that).
I. Determination of Immunoglobin Titre
   The titer of each of the sera samples is defined as the reciprocal of the first serial two-fold dilution that has an OD value that is greater than or equal to twice the background value. The OD values for the control animals are averaged at each dilution and the mean titer for the group is determined.

References referred to hereinbefore are incorporated by reference.

The invention claimed is:

1. A method for producing a mucosal and systemic immune response in a human or animal comprising administering an effective amount of a composition comprising at least one antigen and a TH-1 inducing adjuvant selected from a monophosphoryl lipid and a 3-de-O-acylated monophosphoryl lipid at a sublingual site of the human or animal, wherein the mucosal immune response is an IgA response and the systemic immune response is a serum IgG response, wherein the at least one antigen is derived from a virus, bacterium, prion, neoplasm, autoantigen, animal, plant, recombinant or synthetic material.

2. A method of producing an IgA immune response in a human or animal comprising administering an effective amount of a composition comprising at least one antigen and a TH-1 inducing adjuvant selected from a monophosphoryl lipid and a 3-de-O-acylated monophosphoryl lipid at a sublingual site of the human or animal, wherein the IgA immune response is a mucosal immune response at a site distal from the site of administration, wherein the at least one antigen is derived from a virus, bacterium, prion, neoplasm, autoantigen, animal, plant, recombinant or synthetic material.

3. The method of claim 1, wherein the IgA immune response is distal from the sublingual site of administration of the composition.

4. The method of claim 1, wherein the composition additionally comprises a sublingually administrable diluent, excipient, or carrier.

5. The method of claim 1, wherein the composition comprises an aqueous solution, a gel, a capsule, a lozenge, or a tablet.

6. The method of claim 2, wherein the composition additionally comprises a sublingually administrable diluent, excipient, or carrier.

7. The method of claim 2, wherein the composition comprises an aqueous solution, a gel, a capsule, a lozenge, or a tablet.

* * * * *